United States Patent [19]

Rinehart

[11] 4,120,886

[45] Oct. 17, 1978

[54] S-ARYL N-CYCLOALKYLTHIOLCARBAMATES

[75] Inventor: Jay Kent Rinehart, Akron, Ohio

[73] Assignee: PPG Industries, Inc., Pittsburgh, Pa.

[21] Appl. No.: 842,818

[22] Filed: Oct. 17, 1977

Related U.S. Application Data

[62] Division of Ser. No. 701,382, Jun. 30, 1976, Pat. No. 4,055,656.

[51] Int. Cl.$^2$ ..................... C07C 153/09; A01N 9/12
[52] U.S. Cl. ................................. 260/455 A; 424/300
[58] Field of Search ................................... 260/455 A

[56] References Cited

U.S. PATENT DOCUMENTS 3,932,632   1/1976   Adolphi et al. ............... 260/239 BF

*Primary Examiner*—Lewis Gotts
*Assistant Examiner*—Robert C. Whittenbaugh
*Attorney, Agent, or Firm*—Robert J. Grassi

[57] ABSTRACT

Novel S-aryl N-cycloalkylthiolcarbamates, such as S-4-methoxyphenyl N-cyclohexylthiolcarbamate, which are useful for controlling pea aphids, and the method of controlling pea aphids with the compounds are disclosed.

3 Claims, No Drawings

S-ARYL N-CYCLOALKYLTHIOLCARBAMATES

This is a division of application Ser. No. 701,382, filed June 30, 1976, now U.S. Pat. No. 4,055,656.

BACKGROUND OF THE INVENTION

1. Field of the Invention

This invention pertains to novel S-aryl N-cycloalkylthiolcarbamates, particularly those in which the cycloalkyl has from three to six carbon atoms. A particular example being S-4-methoxyphenyl N-cyclohexylthiolcarbamate. This invention also relates to the method of controlling plant pests with these compounds, particularly pea aphids.

2. Description of the Prior Art

Plant pests such as insects, continually affect the growth of crops, trees, and other desirable vegetation. One method of controlling insects is by application of chemicals which affect the insects. These chemicals are applied to the soil, to the desirable plant, or directly to the insect itself. Because thousands of different insect species exist which differ in tolerance to chemicals, new chemicals must be discovered which are effective to control the deleterious effects of insects.

The prior art shows that certain thiolcarbamates are active against plant pests. The following patents and references illustrate the different thiolcarbamates claimed to be effective against certain plant pests.

U.S. Pat. Nos. 2,977,209 and 3,265,563 disclose S-phenyl N-alkylthiolcarbamates, S-chlorophenyl N-alkylthiolcarbamates, S-ethoxyphenyl N-allylthiolcarbamate, S-ethoxyphenyl N-alkylthiolcarbamates, S-p-tolyl N-alkylthiolcarbamates, and S-2,4-dimethylphenyl N-alkylthiolcarbamates as herbicides and fungicides. U.S. Pat. No. 3,632,332 discloses S-4-methylbenzyl-N,N-diethylthiocarbamate as a herbicide for rice fields. U.S. Pat. No. 3,301,885 discloses S-substituted phenyl N-alkyl, N-alkoxythiolcarbamates as herbicides, miticides, and insecticides. U.S. Pat. No. 3,687,653 discloses trifluoromethylbenzyl N-alkylthiolcarbamates as herbicides. U.S. Pat. No. 3,046,189 and Canadian Pat. No. 789,575 disclose S-alkyl N-alkylthiocarbamates as nematocides. R. Reimschneider and O. Lorenz, in *Monatsch.*, 84, 518 (1953) describe S-phenyl N,N-dimethylthiolcarbamate, and D. G. Crosby and C. Niemann, *Journal of American Chemical Society*, 76, 4458 (1954) describe S-phenyl N-cyclohexylthiolcarbamate, and S-phenyl N-phenylthiolcarbamate. Netherlands Pat. NO. 6,606,753 discloses S-phenyl N-trifluoromethylphenylthiocarbamate and S-substituted phenyl N-substituted trifluoromethylphenylthiocarbamates as anthelmintics. M. S. Newman and H. A. Karnes, *Journal of Organic Chemistry*, 31, 3980–3983 describe S-β-naphthyl N,N-dimethylthiolcarbamate, S-2-nitrophenyl N,N-dimethylthiolcarbamate, S-3-nitrophenyl N,N-dimethylthiolcarbamate, S-2,4,5-trichlorophenyl N,N-dimethylthiolcarbamate, S-3-trifluoromethylphenyl N,N-dimethylthiolcarbamate, S-2,3,5,6-tetramethylpentyl N,N-dimethylthiolcarbamate, S-4-tert-butylphenyl N,N-dimethylthiolcarbamate, S-2-methoxyphenyl N,N-dimethylthiolcarbamate and S-4-methoxyphenyl N,N-dimethylthiocarbamate. U.S. Pat. No. 3,932,632 discloses insecticides of mixtures of dithiophosphate compounds mixed with S-aryl N,N-dialkylthiolcarbamates, or S-aryl N,N-dialkylenethiolcarbamates, or S-aryl N,N-dialkynylthiolcarbamates, S-aryl N,N-(alkyl, alkylene, or alkynyl), (alkyl, alkylene, or alkynyl)thiolcarbamates, where the aryl may be a substituted phenyl.

SUMMARY OF THE INVENTION

This invention pertains to S-aryl N-cycloalkylthiolcarbamates in which the cycloalkyl has from three to six carbon atoms, but 3,4-dichlorophenyl N-cyclohexylthiolcarbamate is known. A particular compound being S-4-methoxyphenyl N-cyclohexylthiolcarbamate.

These compounds are used to control plant pests, namely, insects relating to the Acrythosiphum genus, in particular *Acrythosiphum pisum* (Pea Aphid). The invention also concerns the method of controlling these plant pests with these compounds, particularly by contacting the insects with an effective amount of the compounds.

DESCRIPTION OF THE PREFERRED EMBODIMENTS

The S-aryl N-cycloalkylthiolcarbamates used for the purpose disclosed herein, are represented by the general graphic formula:

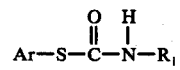

wherein:

Ar is α-naphthyl, β-naphthyl, 4-chlorophenyl, 4-nitrophenyl, 2-chlorophenyl, 4-bromophenyl, 4-fluorophenyl, 3,4-dichlorophenyl, 3,4-dibromophenyl, 3,4-xylyl, 3-alkylphenyl in which the alkyl has from one to four carbon atoms, 4-alkylphenyl in which the alkyl has from one to four carbon atoms, 3-alkoxyphenyl in which the alkoxy has from one to four carbon atoms, 4-alkoxyphenyl in which the alkoxy has from one to four carbon atoms, 3-alkylthiophenyl in which the alkylthio has from one to four carbon atoms, and 4-alkylthiophenyl in which the alkylthio has from one to four carbon atoms; and R is a cycloalkyl having from three to six carbon atoms.

The phrase "3-alkylphenyl in which the alkyl has from one to four carbon atoms" as used herein and in the claims refers to:

3-tolyl, 3-ethylphenyl, 3-n-propylphenyl, 3-isopropylphenyl, 3-n-butylphenyl, 3-sec-butylphenyl, 3-isobutylphenyl, and 3-tert-butylphenyl.

The phrase "4-alkylphenyl in which the alkyl has from one to four carbon atoms" as used herein and in the claims refers to:

4-tolyl, 4-ethylphenyl, 4-n-propylphenyl, 4-isopropylphenyl, 4-n-butylphenyl, 4-sec-butylphenyl, 4-isobutylphenyl, and 4-tert-butylphenyl.

The phrase "3-alkoxyphenyl in which the alkoxy has from one to four carbon atoms" as used herein and in the claims refers to:

3-methoxyphenyl, 3-ethoxyphenyl, 3-n-propoxyphenyl, 3-isopropoxyphenyl, 3-n-butoxyphenyl, 3-sec-butoxyphenyl, 3-isobutoxyphenyl, and 3-tert-butoxyphenyl.

The phrase "4-alkoxyphenyl in which the alkoxy has from one to four carbon atoms" as used herein and in the claims refers to:

4-methoxyphenyl, 4-ethoxyphenyl, 4-n-propoxyphenyl, 4-isopropoxyphenyl, 4-n-butoxyphenyl, 4-sec-butoxyphenyl, 4-isobutoxyphenyl, and 4-tert-butoxyphenyl.

The phrase "3-alkylthiophenyl in which the alkylthio has from one to four carbon atoms" as used herein and in the claims refers to:

3-methylthiophenyl, 3-ethylthiophenyl, 3-n-propylthiophenyl, 3-isopropylthiophenyl, 3-n-butylthiophenyl, 3-sec-butylthiophenyl, 3-isobutylthiophenyl, and 3-tert-butylthiophenyl.

The phrase "4-alkylthiophenyl in which the alkylthio has from one to four carbon atoms" as used herein and in the claims refers to:

4-methylthiophenyl, 4-ethylthiophenyl, 4-n-propylthiophenyl, 4-isopropylthiophenyl, 4-n-butylthiophenyl, 4-sec-butylthiophenyl, 4-isobutylthiophenyl, and 4-tert-butylthiophenyl.

The phrase "cycloalkyl having from three to six carbon atoms" as used herein and in the claims refers to:
cyclopropyl, 2-methylcyclopropyl, cyclobutyl, cyclopentyl, 2-methylcyclopentyl, and cyclohexyl.

Representative compounds of the general formula are:
S-4-chlorophenyl N-cyclopropylthiolcarbamate;
S-4-nitrophenyl N-2-methylcyclopropylthiolcarbamate;
S-2-chlorophenyl N-cyclobutylthiolcarbamate;
S-4-bromophenyl N-cyclopentylthiolcarbamate;
S-4-fluorophenyl N-2-methylcyclopentylthiolcarbamate;
S-3,4-dichlorophenyl N-cyclohexylthiolcarbamate;
S-3,4-dibromophenyl N- cyclopentylthiolcarbamate
S-3,4-xylyl N-2-methylcyclopentylthiolcarbamate;
S-3-methylphenyl N-2-methylcyclopentylthiolcarbamate;
S-3-ethylphenyl N-cyclohexylthiolcarbamate;
S-3-n-propylphenyl N-cyclopropylthiolcarbamate;
S-3-isopropylphenyl N-2-methylcyclopropylthiolcarbamate;
S-3-n-butylphenyl N-2-methylcyclopropylthiolcarbamate;
S-3-sec-butylphenyl N-cyclohexylthiolcarbamate;
S-3-isobutylphenyl N-cyclobutylthiolcarbamate;
S-3-tert-butylphenyl N-2-methylcyclopropylthiolcarbamate;
S-4-methylphenyl N-cyclobutylthiolcarbamate;
S-4-ethylphenyl N-cyclopentylthiolcarbamate;
S-4-n-propylphenyl N-cyclohexylthiolcarbamate;
S-4-isopropylphenyl N-2-methylcyclopentylthiolcarbamate;
S-4-n-butylphenyl N-cyclopropylthiolcarbamate;
S-4-sec-butylphenyl N-cyclohexylthiolcarbamate;
S-4-isobutylphenyl N-cyclopentylthiolcarbamate;
S-4-tert-butylphenyl N-2-methylcyclopentylthiolcarbamate;
S-4-methoxyphenyl N-cyclohexylthiolcarbamate;
S-4-ethoxyphenyl N-2-methylcyclopropylthiolcarbamate;
S-4-n-propoxyphenyl N-cyclobutylthiolcarbamate;
S-4-isopropoxyphenyl N-cyclopropylthiolcarbamate;
S-4-n-butoxyphenyl N-cyclobutylthiolcarbamate;
S-4-isobutoxyphenyl N- cyclopentylthiolcarbamate;
S-4-sec-butoxyphenyl N-2-methylcyclopentylthiolcarbamate;
S-4-tert-butoxyphenyl N-cyclohexylthiolcarbamate;
S-3-methoxyphenyl N-cyclopropylthiolcarbamate;
S-3-ethoxyphenyl N-2-methylcyclopentylthiolcarbamate;
S-3-n-propoxyphenyl N-cyclopropylthiolcarbamate;
S-3-isopropoxyphenyl N-cyclopentylthiolcarbamate;
S-3-n-butoxyphenyl N-2-methylcyclopropylthiolcarbamate;
S-3-sec-butoxyphenyl N-cyclobutylthiolcarbamate;
S-3-isobutoxyphenyl N-cyclopentylthiolcarbamate;
S-3-tert-butoxyphenyl N-2-methylcyclopentylthiolcarbamate;
S-3-methylthiophenyl N-cyclobutylthiolcarbamate;
S-3-ethylthiophenyl N-cyclohexylthiolcarbamate;
S-3-n-propylthiophenyl N-2-methylcyclopropylthiolcarbamate;
S-3-isopropylthiophenyl N-cyclopropylthiolcarbamate;
S-3-n-butylthiophenyl N-cyclobutylthiolcarbamate;
S-3-sec-butylthiophenyl N-cyclopropylthiolcarbamate;
S-3-isobutylthiophenyl N-2-methylcyclopropylthiolcarbamate;
S-3-tert-butylthiophenyl N-2-methylcyclopropylthiolcarbamate;
S-4-methylthiophenyl N-2-methylcyclopropylthiolcarbamate;
S-4-ethylthiophenyl N-cyclobutylthiolcarbamate;
S-4-n-propylthiophenyl N-cyclobutylthiolcarbamate;
S-4-isopropylthiophenyl N-cyclopentylthiolcarbamate;
S-4-n-butylthiophenyl N-methylcyclopentylthiolcarbamate;
S-4-sec-butylthiophenyl N-cyclohexylthiolcarbamate;
S-4-isobutylthiophenyl N-cyclopentylthiolcarbamate; and
S-4-tert-butylthiophenyl N-2-methylcyclopentylthiolcarbamate.

The preferred S-aryl N-cycloalkylthiolcarbamates of the general formula are those in which R is cycloalkyl of cyclopropyl, cyclobutyl, cyclopentyl, or cyclohexyl. Representative compounds of which are:
S-4-chlorophenyl N-cyclopentylthiolcarbamate;
S-4-nitrophenyl N-cyclohexylthiolcarbamate;
S-2-chlorophenyl N-cyclopropylthiolcarbamate;
S-4-bromophenyl N-cyclobutylthiolcarbamate;
S-4-fluorophenyl N-cyclopentylthiolcarbamate;
S-3,4-dichlorophenyl N-cyclohexylthiolcarbamate;
S-3,4-xylyl N-cyclohexylthiolcarbamate;
S-3-tolyl N-cyclopropylthiolcarbamate;
S-3-ethylphenyl N-cyclobutylthiolcarbamate;
S-3-isopropylphenyl N-cyclopentylthiolcarbamate;
S-3-tert-butylphenyl N-cyclohexylthiolcarbamate;
S-4-tolyl N-cyclopropylthiolcarbamate;
S-4-ethylphenyl N-cyclobutylthiolcarbamate;
S-4-isopropylphenyl N-cyclopentylthiolcarbamate;
S-4-tert-butylphenyl N-cyclohexylthiolcarbamate;
S-3-methoxyphenyl N-cyclopropylthiolcarbamate;
S-3-ethoxyphenyl N-cyclobutylthiolcarbamate;
S-3-isopropoxyphenyl N-cyclopentylthiolcarbamate;
S-3-tert-butoxyphenyl N-cyclohexylthiolcarbamate;
S-4-methoxyphenyl N-cyclopropylthiolcarbamate;
S-4-ethoxyphenyl N-cyclobutylthiolcarbamate;
S-4-isopropoxyphenyl N-cyclopentylthiolcarbamate;
S-4-tert-butoxyphenyl N-cyclohexylthiolcarbamate;
S-3-methylthiophenyl N-cyclopropylthiolcarbamate;
S-3-ethylthiophenyl N-cyclobutylthiolcarbamate;
S-3-isopropylthiophenyl N-cyclopentylthiolcarbamate;
S-3-tert-butylthiophenyl N-cyclohexylthiolcarbamate;
S-4-methylthiophenyl N-cyclopropylthiolcarbamate;
S-4-ethylthiophenyl N-cyclobutylthiolcarbamate;
S-4-isopropylthiophenyl N-cyclopentylthiolcarbamate; and
S-4-tert-butylthiophenyl N-cyclohexylthiolcarbamate.

Highly preferred are those S-aryl N-cycloalkylthiolcarbamates of the general formula in which R is cyclohexyl and cyclopropyl.

The preferred aryls of 3-alkylphenyls having from one to four carbon atoms, mentioned herein, are:

3-tolyl, 3-ethylphenyl, 3-isopropylphenyl, and 3-tert-butylphenyl.

The preferred aryls of 4-alkylphenyls having from one to four carbon atoms, mentioned herein, are:
4-tolyl, 4-ethylphenyl, 4-isopropylphenyl, and 4-tert-butylphenyl.

The preferred aryls of 4-alkoxyphenyls having from one to four carbon atoms mentioned herein are:
4-methoxyphenyl, 4-ethoxyphenyl, 4-isopropoxyphenyl, and 4-tert-butoxyphenyl.

The preferred aryls of 3-alkoxyphenyls having from one to four carbon atoms mentioned herein are:
3-methoxyphenyl, 3-ethoxyphenyl, 3-isopropoxyphenyl, and 4-tert-butoxyphenyl.

The preferred aryls of 4-alkylthiophenyls having from one to four carbon atoms mentioned herein are:
4-methylthiophenyl, 4-ethylthiophenyl, 4-isopropylthiophenyl, and 4-tert-butylthiophenyl.

The preferred aryls of 3-alkylthiophenyls having from one to four carbon atoms mentioned herein are:
3-methylthiophenyl, 3-ethylthiophenyl, 3-isopropylthiophenyl, and 3-tert-butylthiophenyl.

Representative examples of these preferred aryls and highly preferred cycloalkyl groups are:
S-4-chlorophenyl N-cyclopropylthiolcarbamate;
S-4-nitrophenyl N-cyclopropythiolcarbamate;
S-2-chlorophenyl N-cyclohexylthiolcarbamate;
S-4-bromophenyl N-cyclopropylthiolcarbamate;
S-4-fluorophenyl N-cyclohexylthiolcarbamate;
S-3,4-dichlorophenyl N-cyclopropylthiolcarbamate;
S-3,4-xylyl N-cyclopropylthiolcarbamate;
S-3-tolyl N-cyclohexylthiolcarbamate;
S-3-ethylphenyl N-cyclopropylthiolcarbamate;
S-3-isopropylphenyl N-cyclohexylthiolcarbamate;
S-3-tert-butylphenyl N-cyclopropylthiolcarbamate;
S-4-tolyl N-cyclohexylthiolcarbamate;
S-4-ethylphenyl N-cyclopropylthiolcarbamate;
S-4-isopropylphenyl N-cyclohexylthiolcarbamate;
S-3-methoxyphenyl N-cyclohexylthiolcarbamate;
S-3-ethoxyphenyl N-cyclopropylthiolcarbamate;
S-3-isopropoxyphenyl N-cyclohexylthiolcarbamate;
S-3-tert-butoxyphenyl N-cyclopropylthiolcarbamate;
S-4-methoxyphenyl N-cyclohexylthiolcarbamate;
S-4-ethoxyphenyl N-cyclopropylthiolcarbamate;
S-4-isopropoxyphenyl N-cyclohexylthiolcarbamate;
S-4-tert-butoxyphenyl N-cyclopropylthiolcarbamate;
S-3-methylthiophenyl N-cyclohexylthiolcarbamate;
S-3-ethylthiophenyl N-cyclopropylthiolcarbamate;
S-3-isopropylthiophenyl N-cyclohexylthiolcarbamate;
S-3-tert-butylthiophenyl N-cyclopropylthiolcarbamate;
S-4-methylthiophenyl N-cyclohexylthiolcarbamate;
S-4-ethylthiophenyl N-cyclopropylthiolcarbamate;
S-4-isopropylthiophenyl N-cyclohexylthiolcarbamate; and
S-4-tert-butylthiophenyl N-cyclopropylthiolcarbamate.

Synthesis of the Compounds

The following example illustrates the synthesis of these compounds by reaction of arylthiols having an aryl group mentioned herein with isocyanates having a cycloalkyl mentioned herein.

EXAMPLE I

SYNTHESIS OF S-4-METHOXYPHENYL N-CYCLOHEXYLTHIOLCARBAMATE

Cyclohexylisocyanate (4.3 grams, 34 millimoles) in anhydrous ethylether (10 milliliters) was slowly added (20 minutes) to a stirred mixture of 4-methoxybenzenethiol (4.5 grams, 32 millimoles) and one to two drops of triethylamine in anhydrous ethylether (50 milliliters). The clear reaction mixture was refluxed for 4 hours, and the ethylether solvent was allowed to evaporate off.

A white crystalline material was obtained (8.5 grams, 100 percent yield) which was recrystallized from benzene (100 milliliters) to give 4.3 grams of crystalline S-4-methoxyphenyl N-cyclohexylthiocarbamate having a melting point of 101.5° to 103.5° C. The infrared spectrum of the material had a N—H band at 327 centimeters$^{-1}$ and a C=O band at 1645 centimeters$-1$.

Analysis for; $C_{14}H_{19}O_2$, S, N. Calculated percentage: C, 63.36; H, 7.22; N, 5.28. Found percentage: C, 63.38, 63.67; H, 6.73, 7.01; N, 5.08.

In lieu of triethylamine, as a catalyst for the reaction synthesis, other tertiary amines such as tripropylamine or tributylamine may be used.

Removal of the solvents and reactants or other impurities from the aryl N-cycloalkylthiolcarbamates such as 4-chlorophenyl N-cyclopropylthiolcarbamate is not necessary except insofar as they interfere with the intended use of the compound such as control of pea aphids. All conventional purification techniques such as recrystallization from solvents, fractional crystallization, washing with one or more solvents, followed by evaporation of the solvents, filtration from the solvents or their equivalents may be used.

Other routes may be used for synthesis of the S-aryl N-cycloalkylthiocarbamates disclosed herein. For example, S-4-tert-butylphenylthiolchloroformate may be formed by the reaction of S-4-tert-butylbenzenethiol and phosgene in the presence of activated carbon as set forth in U.S. Pat. No. 3,165,544. The S-4-tert-butylphenylthiolchloroformate is reacted with a cycloalkylamine having a cycloalkyl mentioned herein, such as cyclopentylamine, an inert solvent mentioned herein in the presence of a stoichiometric amount of an acid acceptor at temperatures from 15° C. to 100° C. to form S-4-tert-butylphenyl N-cyclopentylthiolcarbamate. An example of this synthesis route is described in assignee's copending application S-p-METHOXYPHENYL N,N-DIALLYLTHIOLCARBAMATE and S-p-METHOXYPHENYL N,N-BIS(2,3-DIBROMOPROPYL)THIOLCARBAMATE, Ser. No. 631,802, filed Nov. 3, 1975.

Another alternate route is the reaction of a cycloalkylcarbamoyl chlorides having a cycloalkyl mentioned herein and an arylthiol having an aryl group mentioned herein. The cycloalkylcarbamoyl chlorides are formed by the reaction of a cycloalkylamine having a cycloalkyl mentioned herein, with phosgene. This synthesis route is illustrated in applicant's copending application entitled S-NAPHTHYL N-ALKYLTHIOLCARBAMATES, (TCS-76-22) Ser. No. 701,384, filed June 30, 1976.

PROPERTIES

The novel S-aryl N-cycloalkylthiolcarbamates disclosed herein may be used to control the deleterious effects of insects of the aphid genus (Acrythosiphum), particular pea aphids (*Acrythosiphum pisum*). The following test procedure illustrates this property.

PEA APHID — CONTACT — TEST PROCEDURE

A stock acetone emulsion was prepared, which had 99.75 weight percent of acetone, 0.20 weight percent of sorbitan trioleate (Span 85 ®), and 0.05 weight percent of sorbitan monooleate polyoxyalkylene trioleate (Tween 80 ®). The test compound was dissolved in a portion of the stock acetone emulsion, and deionized water was added to yield a concentrated test solution containing about 10 weight percent acetone, 0.020 weight percent Span 85 ® and 0.0050 weight percent Tween 80 ®, and 1000 parts per million (ppm) of the test compound.

Individually potted Windsor broadbean (*Vicia fabae*) plants, grown under greenhouse conditions, in first true leaf growth stage were used as host plants.

Ten adult pea aphids (*Acrythosiphum pisum*) in a hemispherical wire mesh container were sprayed with the test solution for about 5 seconds with a sprayer equipped with a Tee-Jet 8001-E spray nozzle tip and operating at 20 pounds per square inch, which is sufficient for coating all of the aphids to the point of run off.

The container with the sprayed aphids was then inverted directly over the Windsor broadbean plant, and secured so as to function as a cage over the plant and sprayed aphids. The test unit (plant, sprayed aphids, and wire mesh container) was then removed to the greenhouse and held there for 3 days, during which time the plant was provided with subterranean watering.

At the end of the 3 day holding period, the aphids were observed for mortality and/or abnormal physiological responses, such as sterility, abnormal egg production, or nymphs.

Control plants were prepared as above with pea aphids which were not sprayed.

The effectiveness of the test compound is expressed as percent control calculated as follows:

$$\% \text{ control} = \frac{\text{totals number of dead aphids, nymphs, on all plants}}{\text{total number of aphids, nymphs, on all plants}} \times 100\%$$

A minimum of three replicates were used.

The results of the test procedure using 1000 parts per million (ppm) of the test compound are shown in Table 1. Column 1 of Table 1 gives the example number; column 2 gives the test compound, and column 3 gives the percent control.

TABLE 1

PERCENT CONTROL OF PEA APHIDS - CONTACT - TEST PROCEDURE AT 1000 PARTS PER MILLION (ppm)

| Example No. | Test Compound | Percent Control |
|---|---|---|
| II | S-phenyl N-cyclohexyl-thiolcarbamate[a] | 0 |
| III | S-4-methoxyphenyl N-cyclo-hexylthiolcarbamate | 20 |

[a] known compound described in *Journal of American Chemical Society*, 76, 4458 (1954).

APPLICATION a. Formulations

The novel S-aryl N-cycloalkylthiolcarbamates disclosed herein, such as S-4-methoxyphenyl N-cyclohexylthiolcarbamate, may themselves be directly applied to the aphids or other equivalent insects thereof, or it may be applied to the plants themselves. It is, however, preferable to use suitable agricultural formulations which contain other ingredients which enhance application of this compound. These agricultural formulations will generally comprise from 5 percent to 95 percent by weight of S-4-methoxyphenyl N-cyclopropylthiolcarbamate, or of the other compounds disclosed herein, or mixtures of these compounds, and either from 1 percent to 95 percent by weight of an agricultural diluent, or from 1 percent to 20 percent by weight of a surface active agent and other ingredients required to produce wettable powders, dusts, solutions, emulsifiable concentrates, granules, and the like, or both.

Wettable powders will contain from 25 to 80 percent active ingredients, from 0.1 percent to 5.0 percent wetters and dispersants with the balance consisting of inorganic absorptive diluents.

Since some compounds are solids, others are liquids, and others are viscous materials, they may be dissolved in one or more solvents and then sprayed upon the absorptive diluents of attapulgite clay, synthetic fine silica, and synthetic calcium and sodium alumino-silicates, or other solid insecticides, or foliar fungicides mentioned herein and then the solvent or solvents are evaporated off.

Emulsifiable oils will contain from 20 percent to 97 percent active ingredient, from 3.0 to 10.0 percent of an emulsifying agent, and may also contain from 1 percent to 77 percent water-immiscible solvent such as xylene or alkylated naphthalene.

Granules will contain from 5 percent to 25 percent active ingredient, and may also contain from 1 percent to 20 percent of a surfactant extended upon a granular base such as vermiculite or granular attapulgite. Granules produced by extrusion or tumbling will contain like amounts of active ingredient and surfactant.

For the control of a wider range of crop-pests and diseases it is sometimes desirable to combine S-4-methoxyphenyl N-cyclopropylthiolcarbamate, or S-4-methoxyphenyl N-cyclohexylthiolcarbamate or other compound with from 0.05 to 4 parts by weight of insecticides and fungicides, etc., known to be effective against crop-pests and diseases in concentrated premix or during the application step for foliar applications. Examples of other pesticides are: granules containing stable metal azide-metal salt formulations disclosed in assignee's copending application entitled AZIDE-METAL SALT FORMULATIONS, Ser. No. 624,357, filed Oct. 21, 1975, now abandoned, Sevin 1(naphthyl-N-methylcarbamate), Chlorobenzilate (ethyl 4,4'-dichlorobenzilate), Guthion (O,O-diethyl-S-[4-oxo-1,2,3-benzotriazin-3(4H)-ylmethyl]phosphorodithioate), Disyston (O,O-diethyl-S-[2-(ethylsulfinyl)ethyl]-phosphorodithioate), Maneb (manganous ethylene bis-dithiocarbamate), Karathane (mixture of 2,4-dinitro-6-octylphenylcrotonate, 2,6-dinitro-4-octylphenylcrotonate, nitrooctylphenols (principally dinitro), 4-(1-methylheptyl)2,6-dinitrophenylcrotonate, 4-(1-ethylhexyl)2,6-dinitrophenylcrotonate, 4-(1-propylpentyl)2,6-dinitrophenylcrotonate, 6-(1-methylheptyl)-2,4-dinitrophenylcrotonate, 6-(1-ethylhexyl)2,4-dinitrophenylcrotonate, and 6-(1-propylpentyl)2,4-dinitrophenylcrotonate), Blasticidin (blasticidin-S-benzylaminobenzensulfonate), Benlate (methyl 1-(butylcarbamoyl)-2-benzimidazolecarbamate), or Plantvax (5,6-dihydro-2-methyl-1,4-oxathiin-3-carboxanilide-4,4-dioxide).

In some instances it is also desirable to include special purpose additives which will inhibit corrosion, reduce foaming, reduce caking, or increase flocculation.

The following example illustrates a suitable emulsifiable concentrate formulation for dilution in water for spraying plants, particularly, plant foliage or for application to other plant parts, such as stems, as mentioned herein or directly to the aphids or other insects. In this emulsifiable concentrate formulation, the percents are weight percent.

EXAMPLE IV

| EMULSIFIABLE CONCENTRATE FORMULATIONS | |
|---|---|
| S-4-methoxyphenyl N-cyclohexylthiolcarbamate | 13% |
| Xylene | 41% |
| Isophorone | 41% |
| Atlox 3404* | 1% |
| Atlox 3403 F* | 4% |

*Commercial emulsifier for agricultural pesticides manufactured by Atlas Powder Co., Wilmington, Delaware, and registered with the U.S. Food and Drug Administration.

The concentration of S-4-methoxyphenyl N-cyclohexylthiolcarbamate or S-4-methoxyphenyl N-cyclopropylthiolcarbamate, or other appropriate thiolcarbamate disclosed herein in the emulsifiable concentrate may vary from 5 to 15 weight percent, the xylene may vary from 35 to 45 weight percent, isophorone may vary from 38 to 45 weight percent, Atlox ® 3404 may vary from 0.5 to 3.0 weight percent and Atlox ® 3403 F may vary from 3 to 6 weight percent.

A single compound may be used in the formulation described herein, preferably a plurality of the compounds are used together eitheron a formulation or by concurrent application, that is applying one or more compounds to the soil and one or more of the same or different compounds to the plant itself. In other applications, one or more compounds may be applied to the soil, or the plant, and within about 10 days, one or more of the same compounds, or different compounds may be applied to either the soil or the plant so as to effectively control plant pests.

b. Amount to Apply

When applied as insecticides, an "effective amount" is used, which may be an application rate of from 20 parts per million (ppm) to the amount tolerated by plant, generally from 100 to 20,000 parts per million (ppm) of one or more of the active compounds, applied as a solution to the point of run off, or as a powder or dust which thinly coats the insect or plant part desired to be covered. Normally from 200 parts per million (ppm) to 5000 parts per million (ppm) are used. As used herein or in the claims, an "effective amount" means that amount necessary to achieve effective control of the insect.

c. Method of Application

The method of application is to bring the aphids or other insects into contact with one or more of the novel S-aryl N-cycloalkylthiolcarbamates disclosed herein. The phrase "to bring into contact the insect with an effective amount of a compound of the general formula S-aryl N-cycloalkylthiolcarbamate" as used herein and in the claims refers to any method of application hereby the aphid contacts the compound. Specific ways of achieving this mutual contact are illustrated by the test procedure, and by the following application methods, spraying the plant affected by the aphids, dusting the plants affected by the aphids either before the aphids infest the plant or after the aphids infest the plant.

A single compound may be used in the formulation described herein, preferably a plurality of the compounds are used together either in a formulation or by concured application, that is, applying one or more compounds to the aphids themselves and one or more of the same or different compounds to the plant itself. In ohter applications, one or more compounds may be applied to the aphids, or to the plant, and within about 10 days, one or several of the same compounds, or different compounds may be applied to either the aphids or the plant so as to effectively control the plant pests.

The phrase "effective control" as used herein and in the claims means that control necessary to reduce the deleterious effect of the insect, aphids upon the plants. This may vary from 10 percent control to 100 percent control.

d. Other Uses of the Novel S-aryl N-cycloalkylthiolcarbamates Disclosed Herein The novel S-aryl N-cycloalkylthiolcarbamates disclosed herein, such as S-4-methoxyphenyl N-cyclohexylthiolcarbamate may be used to control the deleterious effects of nematodes upon plants, by systemically applying an effective amount of one or more of the compounds themselves, or in formulations with other compounds used to control other plant pests.

Examples of such nematodes which may be systemically controlled are Meloidogyne species such as *Meloidogyne incognita*, *Meloidogyne exigua* (Coffee Root-knot Nematode), *Meloidogyne arenaria* (Peanut Root-knot Nematode), *Meloidogyne hapla* (Northern Root-knot Nematode), and Citrus root Nematode, or *Ditylonchus destructor* (Potato Rot Nematode). Systemic application means application to the foliage of a plant which plant is deleteriously affected by nematodes such as Meloidogyne species, especially *Meloidogyne incognita* species. In systemic control, S-4-methoxyphenyl N-cyclohexylthiolcarbamate and the other compounds exhibiting systemic nematode control are applied within the vicinity of the infested area, e.g., to the foliage of the plant which has its roots infested by root nematodes, rather than directly to the infested area, e.g., the plant roots themselves.

e. Effective Amount to Apply For Systemic Control of Nematodes

For systemic control of Meloidogyne species, particularly *Meloidogyne incognita*, the effective amount of S-4-methoxyphenyl N-cyclohexylthiolcarbamate and other compounds exhibiting systemic nematode control is a solution containing from 5 ppm to the maximum amount of the component tolerated by the plants applied as a spray to the dripping point. In general it is from 5 ppm to 4,000 ppm, normally from 5 ppm to 500 ppm, and preferably from 5 ppm to 200 ppm.

These same amounts of these compounds, i.e., S-4-methoxyphenyl N-cyclopropylthiolcarbamates are aplied when these compounds are used in combination with insecticides such as Sevin, Chlorobenzilate, Guthion, Disyston, foliar fungicides such as Maneb, Karathane, Blasticidin, Benlate, or Plantvax. The amount of these other insecticides or fungicides will be in accordance with the label instructions disclosed in technical literature given with these known commercial compounds.

While the invention has been described with reference to specific details of certain illustrative embodiments, it is not intended that it shall be limited thereby except insofar as such details appear in the accompanying claims.

I claim:

1. A composition represented by the general formula:

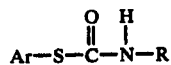
wherein:
Ar is an aryl selected from the group consisting of 4-methoxyphenyl, 4-ethoxyphenyl, 4-isopropoxyphenyl, and 4-tert-butoxyphenyl; and
R is cyclohexyl or cyclopropyl.
2. 4-Methoxyphenyl N-cyclohexylthiolcarbamate.
3. 4-Methoxyphenyl N-cyclopropylthiolcarbamate.
* * * * *